United States Patent
Kern et al.

(10) Patent No.: US 9,802,875 B2
(45) Date of Patent: Oct. 31, 2017

(54) APPARATUS AND PROCESS FOR PREPARING ACETYLENE AND SYNTHESIS GAS

(71) Applicant: BASF SE, Ludwigshafen (DE)

(72) Inventors: Matthias Kern, Deidesheim (DE); Michael Russ, Roemerberg (DE); Peter Renze, Mannheim (DE); Maximilian Vicari, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/915,035

(22) PCT Filed: Aug. 28, 2014

(86) PCT No.: PCT/EP2014/068232
§ 371 (c)(1),
(2) Date: Feb. 26, 2016

(87) PCT Pub. No.: WO2015/028539
PCT Pub. Date: Mar. 5, 2015

(65) Prior Publication Data
US 2016/0207852 A1     Jul. 21, 2016

(30) Foreign Application Priority Data
Aug. 29, 2013 (EP) .................................... 13182176

(51) Int. Cl.
*C09K 3/00*     (2006.01)
*B01J 19/00*     (2006.01)
(Continued)

(52) U.S. Cl.
CPC .................. *C07C 2/78* (2013.01); *B01J 4/002* (2013.01); *B01J 19/2415* (2013.01); *C01B 3/36* (2013.01);
(Continued)

(58) Field of Classification Search
CPC .............. B01J 4/002; B01J 2219/00157; B01J 2219/1941; B01J 2219/24; B01J 19/2415;
(Continued)

(56) References Cited

U.S. PATENT DOCUMENTS 3,176,047 A    3/1965   Braconier et al.
3,396,207 A    8/1968   Bartholomé et al.
(Continued)

FOREIGN PATENT DOCUMENTS

DE        875 198       4/1953
DE     1 051 845       3/1959
(Continued)

OTHER PUBLICATIONS

English translation of International Preliminary Report on Patentability issued Mar. 3, 2016 in PCT/EP2014/068232.
(Continued)

*Primary Examiner* — Colleen Dunn
*Assistant Examiner* — Syed Iqbal
(74) *Attorney, Agent, or Firm* — Oblon, McClelland, Maier & Neustadt, L.L.P.

(57) ABSTRACT

An apparatus (10) for preparation of acetylene and synthesis gas by partial oxidation of hydrocarbons with oxygen is proposed, comprising a reactor (12). The reactor (12) has a burner block (14) with a firing space for acetylene preparation, a secondary space (18) formed within the burner block (14), and an annular space (20) surrounding the secondary space (18). The burner block (14) has holes (22) for supply of a stream of a mixture of hydrocarbons and oxygen to the firing space and holes (24) for supply of a stream of auxiliary oxygen to the firing space. The holes (24) for supply of a stream of auxiliary oxygen to the firing space are connected to the secondary space (18). The secondary space (18) is connected to the annular space (20).

(Continued)

There is a further proposal of a process for preparing acetylene and synthesis gas by partial oxidation of hydrocarbons with oxygen.

13 Claims, 1 Drawing Sheet

(51) Int. Cl.
| | | |
|---|---|---|
| C07C 2/78 | (2006.01) | |
| B01J 4/00 | (2006.01) | |
| B01J 19/24 | (2006.01) | |
| C01B 3/36 | (2006.01) | |

(52) U.S. Cl.
CPC ............... *B01J 2219/00157* (2013.01); *B01J 2219/00247* (2013.01); *B01J 2219/1941* (2013.01); *B01J 2219/24* (2013.01); *C01B 2203/0255* (2013.01); *C01B 2203/062* (2013.01); *C01B 2203/1235* (2013.01)

(58) Field of Classification Search
CPC .... B01J 2219/00247; C01B 2203/0255; C01B 3/36; C01B 2203/1235; C01B 2203/062; C07C 2/78
See application file for complete search history.

(56) References Cited

U.S. PATENT DOCUMENTS

| | | | |
|---|---|---|---|
| 3,674,679 A | 7/1972 | Washimi et al. | |
| 3,843,744 A | 10/1974 | Kramer et al. | |
| 5,789,644 A | 8/1998 | Pässler et al. | |
| 2011/0016790 A1 | 1/2011 | Grossschmidt et al. | |
| 2012/0119150 A1* | 5/2012 | Gro schmidt | ............ B01J 4/004 252/372 |

FOREIGN PATENT DOCUMENTS

| | | | |
|---|---|---|---|
| DE | 1 057 094 | | 5/1959 |
| DE | 1 148 229 | | 5/1963 |
| DE | 2 007 997 | | 9/1970 |
| DE | GB1211569 A | * | 11/1970 |
| DE | 2 307 300 | | 8/1973 |
| DE | 39 04 330 | A1 | 8/1990 |
| DE | 44 22 815 | A1 | 1/1996 |
| GB | 1 211 569 | | 11/1970 |

OTHER PUBLICATIONS

International Search Report Issued Oct. 22, 2014 in PCT/EP14/068232 Filed Aug. 28, 2014.

* cited by examiner

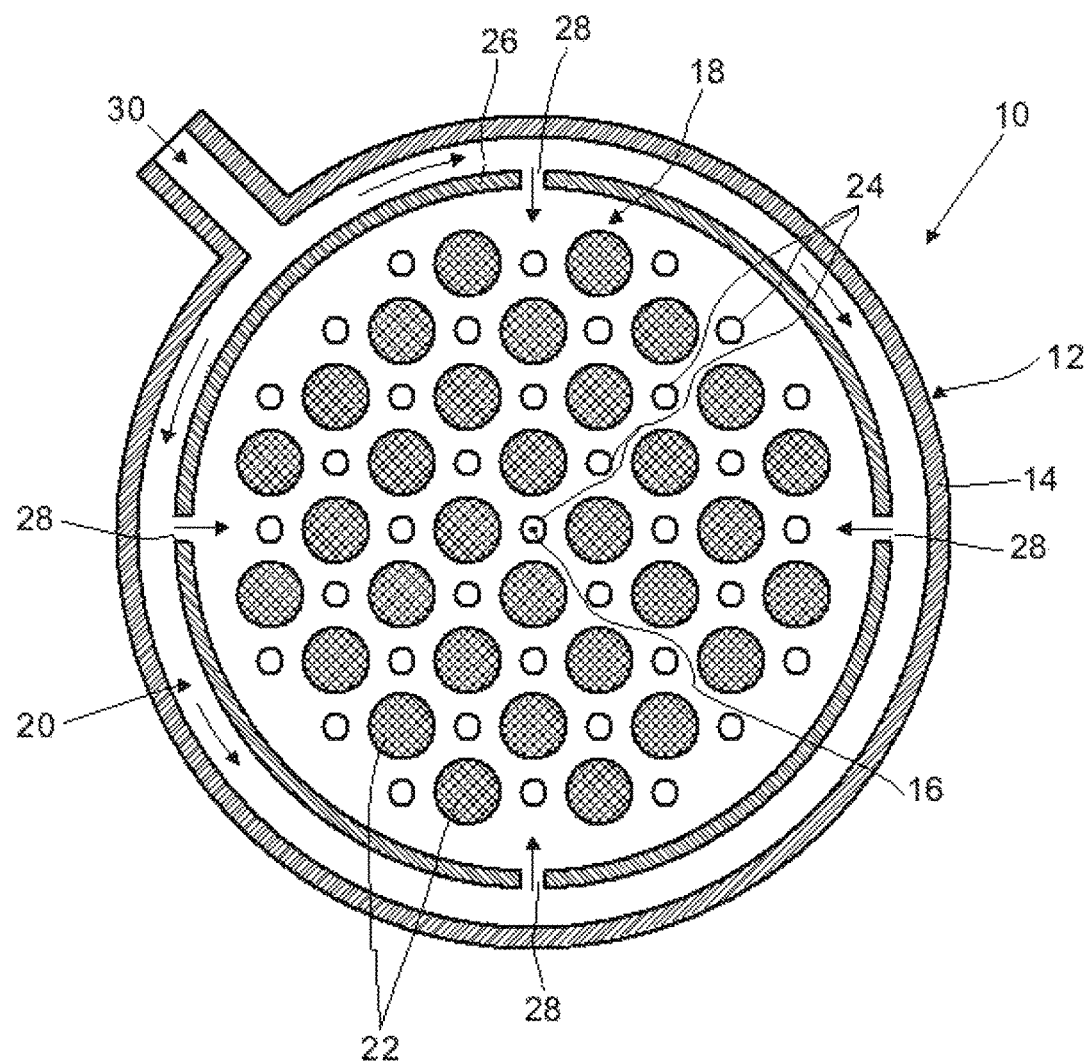

APPARATUS AND PROCESS FOR PREPARING ACETYLENE AND SYNTHESIS GAS

The present invention relates to an improved apparatus and to an improved process for preparing acetylene and synthesis gas by partial oxidation of hydrocarbons in a reactor, in which a stream comprising the hydrocarbon and a stream comprising the oxygen are fed to the reactor.

High-temperature reactions for partial oxidation of hydrocarbons are typically conducted in a reactor system composed of mixing unit, burner block, firing space and quench device. One example of such a partial oxidation in the high-temperature range is the preparation of acetylene and synthesis gas by partial oxidation of hydrocarbons. This is described, for example, in DE 875198, DE 1051845, DE 1057094 and DE 4422815.

These documents elucidate the mixer/burner block/firing space/quench combinations typically used for the BASF-Sachsse-Bartholomé acetylene process—referred to hereinafter, when the combination is being referred to, simply as "reactor".

In this process, the starting materials, for example natural gas and oxygen, are heated separately, typically up to 600° C. In a mixing zone, the reactants are mixed intensively, flow through a burner block and then are reacted exothermically in a firing space. In these cases, the burner block consists of a particular number of parallel channels in which the flow velocity of the ignitable oxygen/natural gas mixture is higher than the flame velocity (reaction rate, conversion rate), in order to prevent the flame from penetrating into the mixing space. The metallic burner block is cooled in order to withstand the thermal stresses. According to the residence time in the mixing space, the risk arises of premature ignition and reignition owing to the limited thermal stability of the mixtures. The term "ignition delay time" or "induction time" is used here to mean that period within which an ignitable mixture does not undergo any significant intrinsic thermal alteration. The induction time depends on the type of hydrocarbons used, the mixing state, pressure and temperature. It determines the maximum residence time of the reactants in the mixing space. Reactants such as hydrogen, liquefied gas or light petroleum, the use of which is particularly desirable owing to enhanced yield and/or capacity in the synthesis process, are notable for a comparatively high reactivity and hence short induction time.

The acetylene burners being used on the present production scale are notable for their cylindrical geometry in the firing space. The burner block preferably has hexagonally arranged passage holes. In one embodiment, for example, 127 holes each having an internal diameter of 27 mm are arranged hexagonally on a circular base cross section with diameter about 500 mm. In general, the hole or channel diameters used are about 19 mm to 27 mm. The downstream firing space in which the flame of the acetylene-forming partial oxidation reaction is stabilized is likewise of cylindrical cross section, is water-cooled and corresponds in terms of appearance to that of a short tube (for example of diameter 180 mm to 533 mm and of length 380 to 450 mm). At the height of the surface of the burner block on the firing space side, what is called auxiliary oxygen is supplied to the reaction space. This ensures flame stabilization and hence a defined distance of the flame root and hence of the commencement of reaction from the stoppage of reaction by the quench unit. The entire burner composed of burner block and firing space is hung from the top of a quench vessel of relatively large cross section by means of a flange. At the height of the exit plane from the firing space, outside the circumference thereof, quench nozzles are installed in one or more quench distributor rings, which atomize the quench medium, for example water or oil, with or without the aid of an atomization medium, and inject the reaction gases leaving the firing space approximately at right angles to the main flow direction. This direct quench has the task of cooling the reacting flow extremely rapidly to about 100° C. (water quench) and 200° C. (oil quench), such that further reactions, especially the degradation of acetylene formed, are frozen. The range and distribution of the quench jets is ideally such that a very substantially homogeneous thermal distribution is achieved within minimum time.

The acetylene burners used on the current production scale are notable for a cylindrical geometry of the firing space. The feedstocks are premixed by means of a diffuser and supplied, with avoidance of backmixing, to the burner block via passage holes in a hexagonal arrangement. In the known processes, the feedstocks are premixed in the mixing diffuser in a relatively large volume and with high preheating temperatures.

The industrial processes described form not only acetylene but essentially hydrogen, carbon monoxide and soot. The soot particles formed in the flame front can adhere as nuclei to the surface of the burner block on the firing space side, which then results in the growth, deposition and baking-on of coke layers, which adversely affects the effectiveness of the process.

In the existing production processes with oil and water quenching, these deposits are periodically removed by mechanical cleaning by means of a stoker unit in the region of the surface of the burner block on the firing space side. For this purpose, complex control of the stoker unit is necessary (Ullmann's Encyclopedia of Industrial Chemistry, 5th Edition, Volume A1, pages 97-144) and, in addition, the particular use time of the mechanism is limited by the thermal stress in the combustion space.

There has been no lack of attempts to avoid the disadvantage of the baking of coke layers onto the surface of the burner block on the firing space side. For instance, the teaching of DE 2307300 discloses the injection of a gaseous substance into the reactor in a region between maximum temperature and quenching site. This is supposed to lead to reactions between the gases added and free radicals, which is supposed to reduce coke formation.

DE 3904330 A1 describes a process for preparing acetylene black by thermal decomposition of acetylene. It is mentioned in this process, which differs significantly from the process for preparing acetylene (e.g. no partial oxidation), that an inert gas stream is optionally introduced.

DE 1148229 describes a process for operating pyrolysis chambers for treatment of hydrocarbons, wherein purging with steam is provided and cooling of the wall is supposed to lead to a water curtain (claim 1). No further information is given about the way in which the purging is executed. The process presented is not a partial oxidation (POx), the purge medium introduced is liquid water, and additional admixing of an oxidizing agent (e.g. oxygen) with the purge medium is not provided. Furthermore, a purge medium is injected only at a maximum of one site in the axial profile of the pyrolysis chamber.

DE 2007997 describes how an oil film on the interior wall of the reaction chamber is supposed to prevent coking. However, an oil film in a firing space tends to coking per se. Therefore, a hydrocarbonaceous (mineral) oil can be ruled out as a purge medium given the present challenge.

The processes disclosed in the documents cited for prevention or reduction of unwanted coke formation, however, are unsatisfactory with respect to effective use in the process for preparing acetylene. For instance, some of the documents, as explained, relate to other reactions where the conditions are quite different and there is no applicability. For instance, the partial oxidation in the process according to the invention is very demanding in terms of characteristics: the residence times play a particularly major role, the stoppage of the reaction must be very exact, and the addition of extraneous substances, including, for example, a purge gas or oxidizer, can move the reaction very rapidly with respect to the site and also the rate thereof, thus leading to a yield loss.

In spite of the advantages brought about by these apparatuses, there is still potential for improvement. As mentioned above, the reactants flow through the burner block through channels or holes in order to be exothermically reacted in a firing space. This section of the burner block is also referred to as perforated burner plate. Thus, to stabilize the partial oxidation reaction front that forms in the context of the Sachsse-Bartholomé acetylene synthesis, auxiliary oxygen is introduced into the firing space or reaction space through individual oxygen lines at predetermined positions along the perforated burner plate of the reactor. These lines are fed to the perforated burner plate radially from the outside. This results in different lengths of the oxygen lines as a result of different distances of the exit orifices of the oxygen lines from the periphery of the perforated burner plate. This results in variation in the pressure drop in the individual oxygen lines that are fed from a common reservoir. If the difference in the lengths of the oxygen lines is too great, there is improper distribution of the oxygen over the perforated burner plate, as a result of which flame stability and the desired yield are no longer assured.

It is therefore an object of the present invention to specify an apparatus and a process for preparing acetylene and synthesis gas, which at least substantially reduces the above-described disadvantages. More particularly, the inventive apparatus is suitable for avoiding improper distribution of the oxygen over the perforated burner plate.

A basic idea of the present invention is to no longer supply the auxiliary oxygen via individual lines, but instead to introduce it into the reaction space by means of a separate distributor ring via an intermediate space through individual holes or channels, the intermediate space being designed, in terms of flow mechanics, such that it ensures homogeneous distribution over the holes that it supplies.

An inventive apparatus for preparing for preparing acetylene and synthesis gas by partial oxidation of hydrocarbons with oxygen comprises a reactor. The reactor has a burner block with a firing space for acetylene preparation, a secondary space formed within the burner block, and an annular space surrounding the secondary space. The burner block has holes for supply of a stream of a mixture of hydrocarbons and oxygen to the firing space and holes for supply of a stream of auxiliary oxygen to the firing space. The holes for supply of a stream of auxiliary oxygen to the firing space are connected to the secondary space. The secondary space is connected to the annular space.

The annular space may surround the secondary space. For example, the annular space surrounds the secondary space concentrically. The annular space may be essentially circular. It should be noted that such a circular form relates to a section view at right angles to the course of a center axis or center line of the annular space. In general, the annular space is cylindrical and the cylinder axis defines the center axis or center line. The secondary space may be separated from the annular space by a wall. The wall may have orifices for connection of the holes for supply of a stream of auxiliary oxygen to the annular space. The orifices may be distributed homogeneously in the wall over the circumference of the burner block. The orifices may have greater cross-sectional area than the holes for supply of a stream of auxiliary oxygen to the firing space. The ratio of the sum total of the cross-sectional areas of the orifices to the cross-sectional area of the annular space may be from 0.05 to 1, for example 0.15. The annular space may be connected to a feed for supply of auxiliary oxygen. The holes for supply of a stream of auxiliary oxygen to the firing space may be arranged in a regular or irregular pattern in the burner block. The ratio of the sum total of the cross-sectional areas of the holes for supply of a stream of auxiliary oxygen to the firing space to the cross-sectional area of the burner block may be from 0.0001 to 0.1, for example 0.015.

A process according to the invention for preparing acetylene and synthesis gas by partial oxidation of hydrocarbons with oxygen comprises the steps which follow. The starting gases, which comprise a hydrocarbonaceous stream and an oxygenous stream, are first preheated separately, then heated in a mixing zone, flow through a burner block and then are reacted in a firing space and subsequently cooled rapidly. Holes and a secondary space are formed in this burner block. The secondary space is connected to the holes and an annular space surrounding the secondary space. The secondary space is formed such that a stream of auxiliary oxygen from the annular space is fed to the firing space in homogeneous distribution through the holes.

The annular space may surround the secondary space. For example, the annular space surrounds the secondary space concentrically. The annular space may be connected to the secondary space via a plurality of orifices, such that the auxiliary oxygen from the annular space is fed to the secondary space in homogeneous distribution. The orifices may be arranged such that the auxiliary oxygen from the annular space is fed into the secondary space in radial direction. The annular space may be fed from a feed for supply of auxiliary oxygen.

Mixing unit, burner block, firing space and quench device conducted. One example of such a partial oxidation in the high-temperature range is the preparation of acetylene and synthesis gas by partial oxidation of hydrocarbons. This is described, for example, in DE 875198, DE 1051845, DE 1057094 and DE 4422815.

These elucidate the mixer/burner block/firing space/quench combinations typically used for the BASF-Sachsse-Bartholomé acetylene process—referred to hereinafter, when the combination is being referred to, simply as "reactor".

In the context of the present invention, a mixing zone or a mixing unit of a reactor is understood to mean that region of the reactor in which the separately heated starting materials, for example natural gas and oxygen, are mixed vigorously.

In the context of the present invention, a burner block of a reactor is understood to mean that region of the reactor through which the heated and mixed starting materials flow. The mixed starting materials flow in channels or holes.

Unless stated otherwise, in the context of the present invention, the expressions "channel" and "hole" are used synonymously. In the context of the present invention, a hole is understood to mean a round or non-round breach in a component.

In the context of the present invention, a firing space of a reactor is understood to mean that region of the reactor into which the heated and mixed starting materials pass after flowing through the burner block and are exothermically reacted. Since, in the context of the present invention, the starting materials used are hydrocarbons and oxygen, this exothermic reaction forms mainly acetylene. By-products formed are hydrogen, carbon monoxide and, to a small extent, soot.

In the context of the present invention, a cross-sectional area is understood to mean the surface area of the area exposed in a cross section. This cross section runs at right angles to a center line of that component whose cross-sectional area is being referred to. For example, the cross-sectional area of an orifice is that surface area which can be found in the case of a cross section at right angles to a theoretical center line through the center of the orifice. The cross sectional area of an annular space is that surface area which can be found in the case of a cross section at right angles to the center line thereof, parallel to which the space extends in the form of a ring. The cross-sectional area of a burner block is that surface area which can be found in the case of a cross section at right angles to the center line thereof, which extends parallel to a direction of longitudinal extent of the burner block. This direction of longitudinal extent is a direction parallel to a cylinder axis of the burner block, since the latter is typically cylindrical in shape. Since the burner block is especially rotationally symmetric in shape, the direction of longitudinal extent is parallel to an axis of rotation of the burner block or of the burner shell.

In the context of the present invention, a regular pattern is understood to mean a pattern consisting of various elements in a predetermined symmetric or homogeneous order. In other words, the elements are arranged repeatedly at fixed spatial distances from one another.

Further optional details and features of the present invention are apparent from the description of preferred working examples which follows, and these are shown schematically in the drawings.

The figure shows:

FIG. 1 a perspective cross-sectional view of an inventive apparatus for preparing acetylene and synthesis gas by partial oxidation of hydrocarbons with oxygen.

EMBODIMENTS OF THE INVENTION

FIG. 1 shows a cross-section view of an apparatus 10 for preparing acetylene and synthesis gas by partial oxidation of hydrocarbons with oxygen. The apparatus 10 comprises a reactor 12.

The reactor 12 has a burner block 14 with a firing space, not shown in detail, for acetylene preparation. The burner block is cylindrical in shape, and so it has a center line 16 corresponding to a cylinder axis of the cylindrical shape. The reactor 12 also has a secondary space 18. The secondary space 18 is formed within the burner block 14. The reactor 12 also has an annular space 20. The annular space 20 surrounds the secondary space 18. For example, the annular space 20 surrounds the secondary space 18 concentrically. The annular space 20, in the working example shown in FIG. 1, is essentially circular, based on the section diagram in FIG. 1. In fact, the annular space 20 is cylindrical when viewed in three dimensions. The section in FIG. 1 runs at right angles to the center line 16 through the burner block 14. The firing space in the section diagram in FIG. 1 is beneath the plane of the drawing, and so it is hidden by the burner block 14 and therefore cannot be seen in FIG. 1.

The burner block 14 has holes 22 for supply of a stream of a mixture of hydrocarbons and oxygen to the firing space. The holes 22 for supply of a stream of a mixture of hydrocarbons and oxygen to the firing space are arranged in a regular pattern in the burner block 14. In the working example shown in FIG. 1, the holes 22 for supply of a stream of a mixture of hydrocarbons and oxygen to the firing space are arranged around the center line 16 analogously to the corners of a square, such that the center line 16 runs through the center of the square. This arrangement is elucidated in detail by way of example for the four innermost holes 22 for supply of a stream of a mixture of hydrocarbons and oxygen to the firing space, with respect to the center line 16. The centers of these four innermost holes 22 form a square, with the center line 16 running through the center of the square. Accordingly, the distance between the centers of two immediately adjacent holes 22, i.e. holes 22 at the ends of an edge of the square is a factor of $\sqrt{2}$ greater than that distance between the centers of two holes 22 opposite one another with the center of the square between them, i.e. holes 22 at the ends of a diagonal of the square. The other holes 22 are arranged analogously, such that the centers of four holes 22 always form a corresponding square.

The burner block 14 also has holes 24 for supply of a stream of auxiliary oxygen to the firing space. The holes 24 for supply of a stream of auxiliary oxygen to the firing space are connected to the secondary space 18. The holes 24 for supply of a stream of auxiliary oxygen to the firing space are likewise arranged in a regular pattern in the burner block 14. Alternatively, the holes 24 for supply of a stream of auxiliary oxygen to the firing space may be arranged in an irregular pattern. In the working example shown in FIG. 1, the holes 24 for supply of a stream of auxiliary oxygen to the firing space are arranged in gaps between the holes 22 for supply of a stream of a mixture of hydrocarbons and oxygen to the firing space. The innermost hole 24 with respect to the center line 16 is arranged such that the center line 16 runs through the center of the innermost hole 24. The holes 24 are arranged analogously to the corners of a square, with the holes 22 for supply of a stream of a mixture of hydrocarbons and oxygen to the firing space between them. This arrangement is elucidated in detail, by way of example, four holes 24. The centers of these four holes 24 form a square, the center of the hole 22 coinciding with the center of the square. Accordingly, the distance between the centers of two immediately adjacent holes 24, i.e. holes 24 at the ends of one edge of the square is greater by a factor of $\sqrt{2}$ than the distance between the centers of two holes 24 opposite one another with the center of the hole 22 or of the square between them, i.e. holes 24 at the ends of a diagonal of the square. The other holes 24 are arranged analogously, such that the centers of four holes 24 always form a corresponding square.

The secondary space 18 is connected to the annular space 20. For example, the secondary space 18 is separated from the annular space 20 by a wall 26. The wall 26 has orifices 28 for connection of the holes 24 for supply of a stream of auxiliary oxygen to the annular space 20. For example, the orifices 28 are arranged in the wall 26 in homogeneous distribution about the center line 16 along a circumferential direction of the burner block 14. In the working example shown in FIG. 1, four orifices 28 are provided, which are arranged with homogeneous spacing along a circumferential direction of the burner block 14, i.e. at a separation of 90° based on the circular form of the annular space 20. The orifices 28 are, as shown in FIG. 1, arranged such that auxiliary oxygen can be fed from the annular space 20 into the secondary space 18 in radial direction based on the center line 16. The orifices 28 have a greater cross-sectional area than the holes 24 for supply of auxiliary oxygen to the firing space. The cross-sectional area of the holes 24 for supply of auxiliary oxygen to the firing space is the surface area of the holes 24 for supply of auxiliary oxygen to the firing space at right angles to the center line 16 or parallel to the plane of the drawing of FIG. 1. The cross-sectional area of an orifice 28 is the surface area of the orifice 28 parallel to the center line 16 or at right angles to the plane of the drawing of FIG. 1 or at right angles to the flow direction of oxygen fed in through the orifice 28. The ratio of the sum total of the cross-sectional areas of the orifices 28 to the cross-sectional area of the annular space 20 may be from 0.05 to 1, preferably from 0.1 to 0.4 and even more preferably from 0.1 to 0.2, for example 0.15. The cross-sectional area of the annular space 20 is the surface area of the annular space 20 parallel to the center line 16 or at right angles to the plane of the drawing of FIG. 1 or at right angles to the flow direction of oxygen flowing through the annular space 20. The ratio of the sum total of the cross-sectional areas of the holes 24 for supply of a stream of auxiliary oxygen to the firing space 16 to the cross-sectional area of the burner block 14 may be from 0.0001 to 0.1, preferably from 0.05 to 0.01 and even more preferably from 0.02 to 0.01, for example 0.015. The cross-sectional area of the burner block 14 is the surface area of the burner block 14 at right angles to the center line 16 or parallel to the plane of the drawing of FIG. 1.

The annular space 20 is connected to a feed 30 for supply of auxiliary oxygen. The feed 30 is fed, for example, from a reservoir, not shown in detail, which may take the form of an oxygen line. For example, the reservoir is an oxygen line installed in a fixed manner from an air separation plant. In this way, in the case of supply of auxiliary oxygen from the annular space 20 to the secondary space 18, it is not possible for more auxiliary oxygen from the annular space 20 to escape into the secondary space 18 than passes from the reservoir through the feed into the annular space 20. This particular geometric configuration thus avoids pressure variations in the annular space 20. It is emphasized explicitly that it is also possible for more than one feed 30 to be connected to the annular space 20.

Consequently, the auxiliary oxygen from the annular space 20 is first fed to the secondary space 18, where the auxiliary oxygen is distributed homogeneously, since, in contrast to the known apparatuses from the prior art, it is not conducted in lines. Since the orifices 28 each have a greater cross-sectional area than the holes 24 for supply of auxiliary oxygen to the firing space, in the case of supply of auxiliary oxygen from the secondary space 18 through the holes 24 for supply of auxiliary oxygen to the firing space into the firing space, it is not possible for more auxiliary oxygen from the secondary space 18 to escape into the firing space than passes from the annular space 20 through the orifices 28 into the secondary space 18. This particular geometric configuration thus avoids pressure variations in the secondary space 18.

The secondary space 18 is thus designed, in terms of flow mechanics, such that it ensures homogeneous distribution between the holes 24 for supply of auxiliary oxygen to the firing space which are supplied by the secondary space 18. Accordingly, variations in the pressure are avoided and the flame stability and the desired yield are improved.

A process according to the invention for preparing acetylene and synthesis gas by partial oxidation of hydrocarbons with oxygen will now be described hereinafter. The underlying process is based on the BASF-Sachsse-Bartholomé acetylene process, and therefore details in this regard will not be addressed in detail, reference instead being made to the abovementioned publications, the contents of which with regard to the process for preparing acetylene and synthesis gas by partial oxidation of hydrocarbons with oxygen are incorporated herein by reference.

The starting gases comprise a hydrocarbonaceous stream, for example a stream of natural gas, and an oxygenous stream, for example a stream of pure oxygen. These starting gases are first preheated separately from one another. Subsequently, the preheated starting gases are heated in a mixing zone, which is not shown in detail. The already heated and mixed starting gases flow through the burner block 14 through the holes 22 for supply of a stream of a mixture of hydrocarbons and oxygen to the firing space, and thus pass into the firing space. In addition, the annular space 20 is fed by the feed 30 with auxiliary oxygen from the reservoir. The auxiliary oxygen then flows through the orifices 28 in the wall 26 into the secondary space 18. Since a plurality of orifices 28 distributed in the wall 26 are provided, the auxiliary oxygen is fed to the secondary space 18 from a plurality of directions. Since the auxiliary oxygen, in contrast to the known prior art apparatuses, is not conducted in lines, the auxiliary oxygen is distributed homogeneously in the secondary space 18. This is also promoted by the orifices 28, which are arranged such that the auxiliary oxygen from the annular space 20 is fed into the secondary space 18 in radial direction based on the center line 16. The auxiliary oxygen then flows out of the secondary space 18 through the holes 24 for supply of auxiliary oxygen to the firing space into the firing space. After flowing through the burner block 14, the starting gases are reacted in the firing space and then cooled rapidly by a quench unit. In addition, the auxiliary oxygen is fed through the feed 30 into the annular space 20, such that it is fed permanently when auxiliary oxygen is withdrawn from the annular space 20 into the secondary space 18.

Consequently, the auxiliary oxygen is thus first fed from the annular space 20 to the secondary space 18, where the oxygen is distributed homogeneously. Through the holes 24 formed in the burner block 14, the oxygen is introduced into the firing space. The secondary space 18 is designed, in terms of flow mechanics, such that it ensures homogeneous distribution between the holes 24 that it supplies. Accordingly, variations in the pressure are avoided and the flame stability and the desired yield are improved.

LIST OF REFERENCE NUMERALS 10 apparatus
12 reactor
14 burner block
16 center line
18 secondary space
20 annular space
22 holes
24 holes
26 wall
28 orifices
30 feed

The invention claimed is:
1. An apparatus, comprising a reactor,
wherein the reactor has a burner block with a firing space for acetylene preparation, a secondary space formed within the burner block, and an annular space surrounding the secondary space, wherein the burner block has holes for supply of a stream of a mixture of hydrocarbons and oxygen to the firing space and holes for supply of a stream of auxiliary oxygen to the firing space, wherein the holes for supply of a stream of auxiliary oxygen to the firing space are connected to the secondary space, wherein the secondary space is connected to the annular space, wherein the secondary space is separated from the annular space by a wall, said wall having orifices to connect the holes for supply of a stream of auxiliary oxygen to the annular space, wherein the annular space is connected to at least one feed for supply of auxiliary oxygen.

2. The apparatus according to claim 1, wherein the annular space concentrically surrounds the secondary space.

3. The apparatus according to claim 1, wherein the annular space is essentially circular.

4. The apparatus according to claim 1, wherein the orifices are distributed homogeneously in the wall along a circumference of the burner block.

5. The apparatus according to claim 1, wherein the orifices have a greater cross-sectional area than the holes for supply of a stream of auxiliary oxygen to the firing space with the annular space.

6. The apparatus according to claim 1, wherein ratio of a sum total of cross-sectional areas of the orifices to a cross-sectional area of the annular space is from 0.05 to 1.

7. The apparatus according to claim 1, wherein the holes for supply of a stream of auxiliary oxygen to the firing space are arranged in a regular or irregular pattern in the burner block.

8. The apparatus according to claim 1, wherein a ratio of a sum total of cross-sectional areas of the holes for supply of a stream of auxiliary oxygen to the firing space to a cross-sectional area of the burner block is from 0.0001 to 0.1.

9. A process for preparing acetylene and synthesis gas by partial oxidation of hydrocarbons with oxygen, the process comprising:

first preheating separately, starting gases, which comprise a hydrocarbonaceous stream and an oxygenous stream;

then heating the starting gases in a mixing zone, flowing the starting gases through a burner block; and then reacting the starting gases in a firing space and subsequently cooling rapidly, wherein holes and a secondary space are formed in the burner block, wherein the secondary space is connected to the holes and an annular space surrounding the secondary space, wherein the secondary space is formed such that a stream of auxiliary oxygen from the annular space is fed to the firing space in homogeneous distribution through the holes.

10. The process according to claim 9, wherein the annular space concentrically surrounds the secondary space.

11. The process according to claim 9, wherein the annular space is connected to the secondary space via a plurality of orifices such that the auxiliary oxygen from the annular space is fed to the secondary space in homogeneous distribution.

12. The process according to claim 9, wherein the annular space is connected to the secondary space via a plurality of orifices, which are arranged such that the auxiliary oxygen from the annular space is fed into the secondary space in radial direction.

13. The process according to claim 9, wherein the annular space is fed from at least one feed for supply of auxiliary oxygen.

* * * * *